United States Patent [19]

Evers et al.

[11] 4,070,308
[45] Jan. 24, 1978

[54] α-OXY(OXO)MERCAPTAN PERFUME AND COLOGNE COMPOSITIONS

[75] Inventors: William J. Evers, Red Bank; Howard H. Heinsohn, Jr., Hazlet; Frederick Louis Schmitt, Holmdel, all of N.J.

[73] Assignee: International Flavors & Fragrances Inc., New York, N.Y.

[21] Appl. No.: 723,529

[22] Filed: Sept. 15, 1976

[51] Int. Cl.$^2$ .............................................. C11B 9/00
[52] U.S. Cl. ................................ 252/522; 260/593 R; 260/609 R; 252/89 R; 252/108; 252/173; 252/368; 424/70; 424/73
[58] Field of Search ...................... 252/522; 260/593 R

[56] References Cited

U.S. PATENT DOCUMENTS

| | | | |
|---|---|---|---|
| 2,888,487 | 5/1959 | Asinger et al. | 260/593 R |
| 3,773,524 | 11/1973 | Katz et al. | 260/593 R |
| 3,948,816 | 4/1976 | Helmlinger et al. | 252/522 |
| 3,950,429 | 4/1976 | Lamparsky et al. | 260/522 |
| 3,952,062 | 4/1976 | Lamparsky et al. | 260/522 |
| 3,954,843 | 5/1976 | Helmlinger et al. | 252/522 |
| 3,966,989 | 6/1976 | Pittet et al. | 252/522 |
| 3,975,311 | 8/1976 | Helmlinger et al. | 252/522 |

*Primary Examiner*—Veronica O'Keefe
*Attorney, Agent, or Firm*—Arthur L. Liberman; Franklin D. Wolffe

[57] ABSTRACT

Perfume and fragrance compositions and perfumed articles including soaps, detergents, powders as well as colognes containing α-oxy(oxo)mercaptans having the structure:

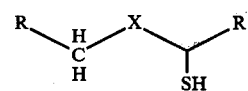

wherein R is any of ethyl, 1-propyl, 2-propyl or 1-butyl; and X is one of:

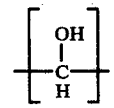

or

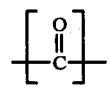

which imparts thereto grapefruit-like, green fruity, concord grape and buchu-leaf oil-like aromas.

12 Claims, 16 Drawing Figures

NMR SPECTRUM FOR EXAMPLE I-(b)

IR SPECTRUM FOR EXAMPLE I-(b)

NMR SPECTRUM FOR EXAMPLE II (b)

IR SPECTRUM FOR EXAMPLE II (c)

NMR SPECTRUM FOR EXAMPLE II (c)

IR SPECTRUM FOR EXAMPLE II (c)

NMR SPECTRUM FOR EXAMPLE III (b)

5-MERCAPTO-6-UNDECANONE

SOLVENT: $CDCl_3$
SWEEP WIDTH: 2000 Hz.

IR SPECTRUM FOR EXAMPLE III (b)

FIG.11
NMR SPECTRUM FOR EXAMPLE III (c)
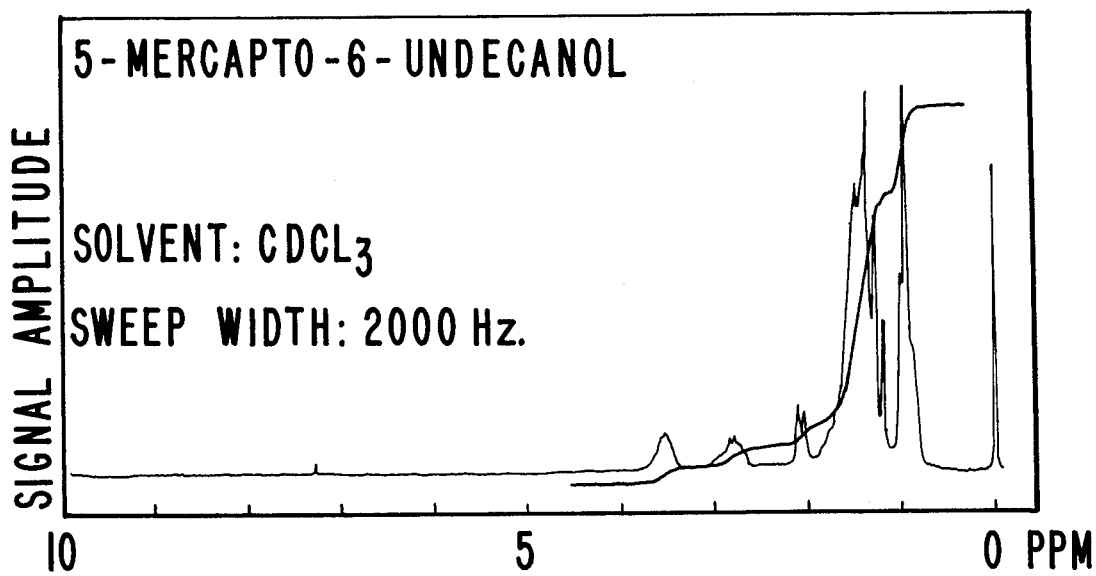
IR SPECTRUM FOR EXAMPLE III (c)
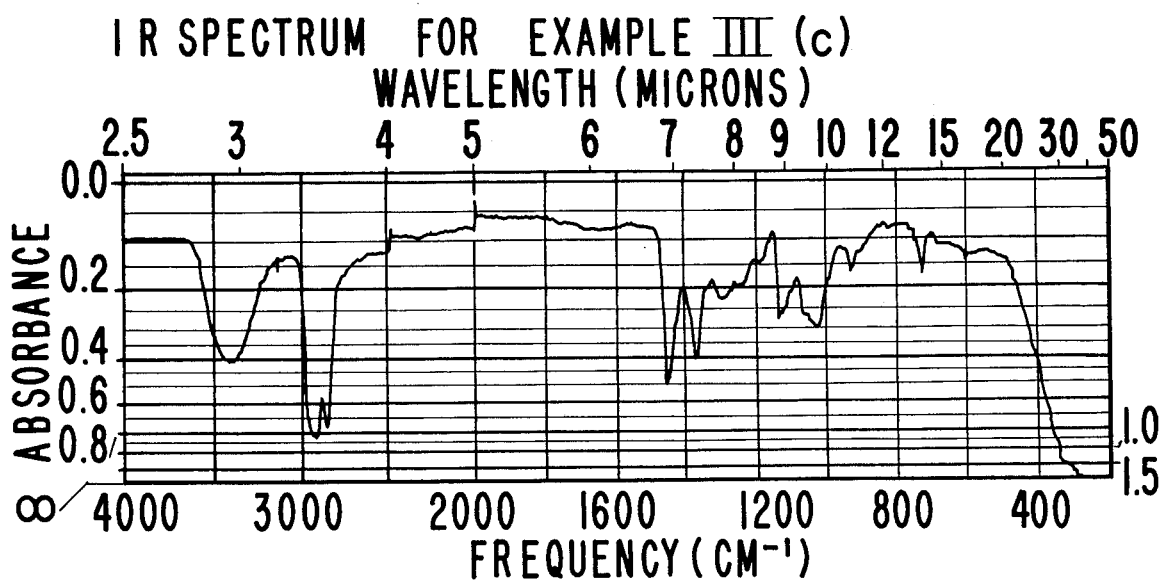
FIG.12

FIG.13
NMR SPECTRUM FOR EXAMPLE IV (b)
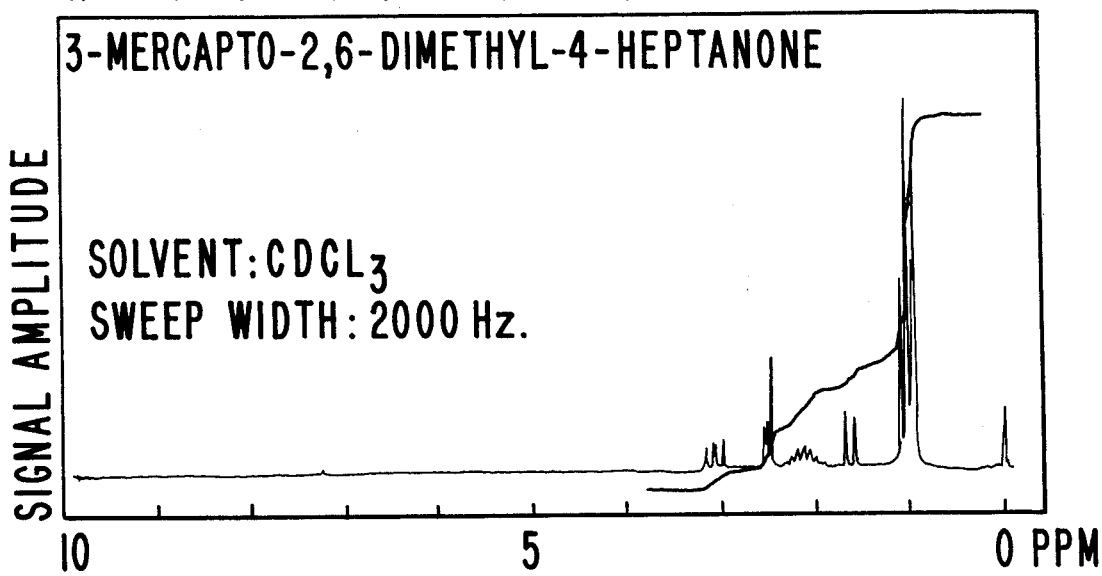
3-MERCAPTO-2,6-DIMETHYL-4-HEPTANONE
SOLVENT: CDCL₃
SWEEP WIDTH: 2000 Hz.
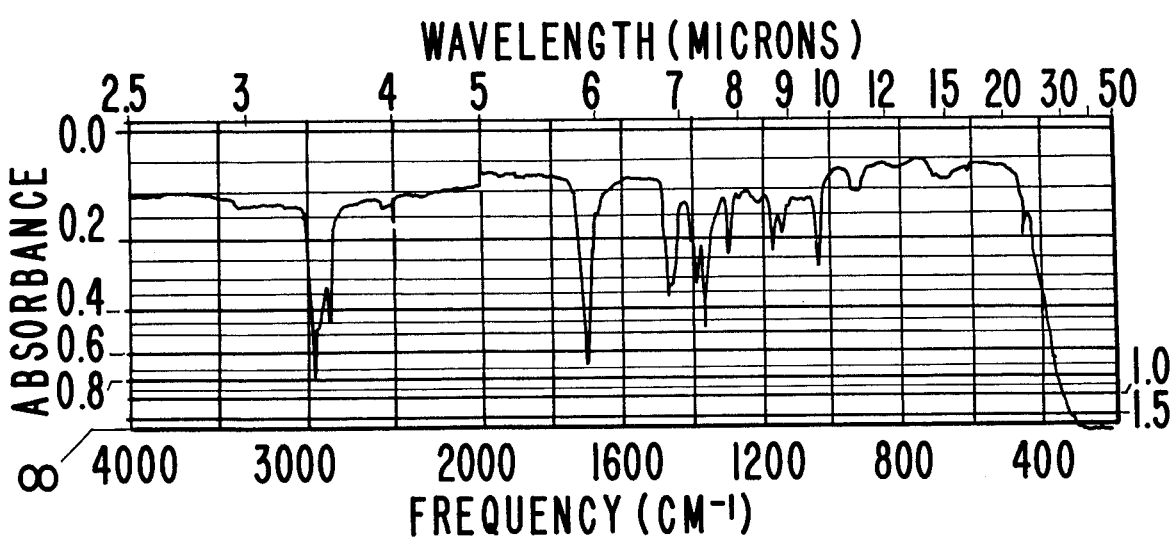
FIG.14

α-OXY(OXO)MERCAPTAN PERFUME AND COLOGNE COMPOSITIONS

BACKGROUND OF THE INVENTION

There is a continuing search for materials having desirable fragrance properties. Such materials are sought either to replace costly natural materials or to provide new fragrances or perfume types which have not heretofore been available. Especially desirable qualities for substances having interesting petitgrain-type fragrances and lavender-type fragrances are stability and persistence, particularly in a wide variety of perfumed articles (e.g. soaps, detergents and powders), perfume compositions and colognes, ease of manufacture, and intensity of aroma.

Prior to this last decade, it was the general opinion among those skilled in the art that compounds containing the mercapto or —SH moiety were not desirable for use in conjunction with fragrance materials and perfumed articles, such as soaps, detergents and powders. However, within the last decade such compounds have been ascertained to be highly useful in perfumery. Thus, for example, Canadian Pat. No. 983,050, issued on Feb. 3, 1976 teaches that 3,7-dimethyl-octa-2,6-dienyl-mercaptan (thiogeraniol) of the formula:

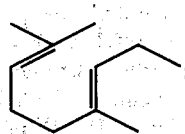

is used in making up a "synthetic buchu leaf oil" and imparts to a lavender type composition a greener and more herbal fragrance. USSR Pat. No. 345,677 teaches that para-menthane-8-thiol-3-one is useful as a synthetic blackcurrent flavoring for foodstuffs. This compound has the structure:

German Offenlegungschrift Pat. No. 2,316,456, published on Oct. 11, 1973 discloses the use of certain thio alcohols or their corresponding esters in perfumery and in perfumed articles, such as detergents, cosmetics and waxes. Such mercapto alcohols having the generic structure:

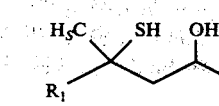

wherein $R_1$ is a hydrocarbon moiety having from 1 up to 7 carbon atoms and $R_2$ is one of hydrogen, methyl or ethyl.

However, no disclosure of the prior art contains a teaching to the effect that compounds having the generic structure:

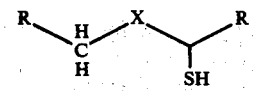

wherein R is one of ethyl, 1-propyl, 2-propyl or 1-butyl; and X is one of:

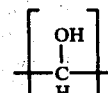

or

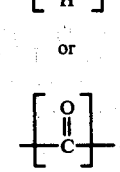

has the ability to create an intense grapefruit, and/or green fruity and/or concord grape and/or buchu leaf oil-like aromas as is carried out in the instant invention. Furthermore, other mercaptans in the prior art, which are shown to be useful in perfumery are indicated to have berry or floral like fragrances, e.g. ionone and irone derivatives having the structure:

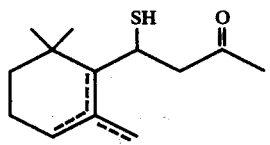

as disclosed in British Pat. No. 1,327,320, published on Aug. 22, 1973 (wherein one of the dashed lines represents a double bond).

Certain α-oxy(oxo)mercaptans are disclosed in the prior art, but their uses in perfumery, in perfumed articles or in colognes are not disclosed. Thus, U.S. Pat. No. 3,773,524, issued on Nov. 20, 1973, discloses the use of α-ketothiols of the formula:

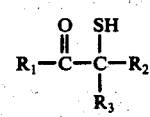

wherein $R_1$ is methyl or ethyl; and $R_2$ and $R_3$ are hydrogen, methyl or ethyl to alter the meat flavor and aroma of foodstuffs. U.S. Pat. No. 3,892,878, issued on July 1, 1975, discloses the use of certain α-hydroxymercaptoalkanes to alter the flavor of foodstuffs, for example, 2-mercapto-3-butanol used in meat flavors. The genus disclosed by U.S. Pat. No. 3,892,878 as follows:

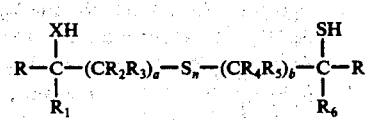

or

-continued

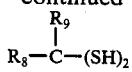

wherein X is oxygen or sulfur, n is 0 or 1, $R_1$-$R_7$ are the same or different and each is hydrogen or lower alkyl of 1-4 carbon atoms, a and b are the same or different and each represents an integer of from 0 to 10 when n is 0 and when n is 1, a and b are the same or different and each represents an integer of from 1 to 10. 3-mercaptoheptanone-4 is disclosed per se in U.S. Pat. No. 2,888,487, issued on May 26, 1959. 3-mercapto-2,6-dimethyl-heptan-4-one is disclosed in Chem. Abstracts 6478 (d) Vol. 62, 1965 (abstract of Asinger, Diem and Schaefer, Monatsch. Chem. 95 (4-5), 1335-54 (1964). Beilstein E-IV-1 discloses 2-mercapto-2,4-dimethyl-pentan-3-one at page 4039, 1-mercapto-octan-2-one at page 4040, and 1-mercapto-nonan-2-one at page 4052 and 1-mercapto-undecan-2-one at page 4060.

THE INVENTION

The invention comprises the novel compositions, perfumed articles and colognes containing α-oxy(oxo)-mercaptans having the structure:

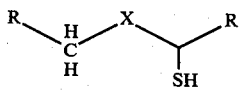

wherein X is one of:

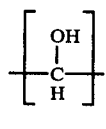

or

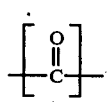

and R is one of ethyl, 1-propyl, 2-propyl or 1-butyl; and processes for manufacturing such compositions, perfumed articles and colognes, the specific embodiments of which are described hereinafter by way of example and in accordance with which it is now preferred to practice the invention.

Briefly, the present invention provides the α-oxy(oxo)mercaptans having the structure:

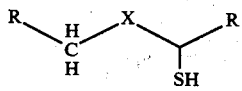

in perfume and fragrance modifying materials and perfumed articles including soaps, detergents and powders, as well as colognes.

Such α-oxy(oxo)mercaptans are obtained by reacting an alkanone with $SO_2Cl_2$ to form an α-chloroalkanone; reacting the α-chloroalkanone with an alkali metal hydrosulfide to form an α-mercaptoalkanone which can be used for its perfumery properties; and, if desired, reacting the α-mercaptoalkanone with a reducing agent such as an alkali metal borohydride in order to obtain an α-hydroxymercaptoalkane. Thus, the aforementioned reaction sequence is illustrated as follows:

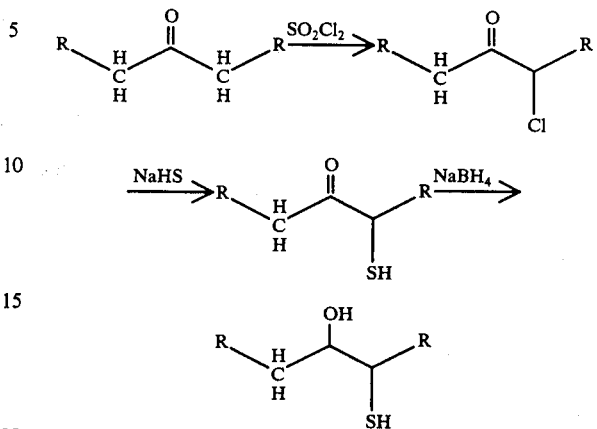

wherein R is one of ethyl, 1-propyl, 2-propyl or 1-butyl.

The reaction between the $SO_2Cl_2$ and ketone preferably takes place in the absence of a solvent at a temperature of between 15° and 40° C. The $SO_2Cl_2$ is preferably added to the ketone. At the end of the reaction, the reaction mass is worked up, the chlorinated ketone being distilled in vacuo.

The resulting chlorinated ketone is preferably reacted with sodium hydrosulfide, which is pre-prepared by reaction of hydrogen sulfide with sodium methylate in methanol. The chlorinated ketone is preferably contained in an inert solvent, e.g., in methanolic solution. Preferably the solution of chlorinated ketone is slowly added simultaneously with the addition of hydrogen sulfide to the sodium methylate solution at a temperature of between 0° and about 10° C; preferably between 0° and 4° C. At the end of the reaction, the reaction mass is concentrated, quenched with water, and made alkaline. After insoluble products are extracted, the reaction mass is acidified to a pH of between 1 and 3 at which time it is extracted with a solvent such as methylene chloride. The resulting extract is then worked up using evaporation and distillation techniques whereupon the α-mercaptoalkanone is recovered. The resulting α-mercaptoalkanone is then used for its perfumery properties; or it may be further reacted with a reducing agent such as sodium borohydride. The reaction with sodium borohydride takes place in an inert solvent such as anhydrous ethanol at a temperature of between 20° and 35° C. A solution in anhydrous ethanol of the α-mercaptoalkanone is added to a solution in anhydrous ethanol of sodium borohydride. The reaction is carried out over a period of time of between 2 and 10 hours. At the end of the reaction, the reaction mass is concentrated and is then admixed with water. The resulting mixture is acidified to a pH of between 1 and 3 and is then extracted with an inert extraction solvent such as methylene chloride. The methylene chloride extract is then dried, evaporated and the resulting α-mercaptoalkanol is then distilled in vacuo or isolated by GLC trapping.

Specific examples of α-oxy(oxo)mercaptans produced using the aforementioned process and their perfumery properties are as follows (as set forth in Table I, below):

TABLE I

| COMPOUND | STRUCTURE | AROMA |
| --- | --- | --- |
| 3-mercapto-4-heptanone | 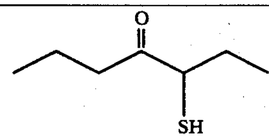 | Strong, green, buchu, grapefruit character with a cassis note. |
| 3-mercapto-4-heptanol | 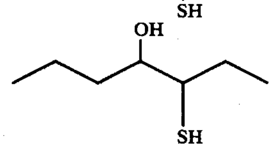 | Strong, buchu, grapefruit character. |
| 4-mercapto-5-nonanone | 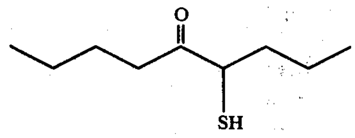 | Green, fruity, grapefruit aroma with minty and leafy nuances. |
| 4-mercapto-5-nonanol | 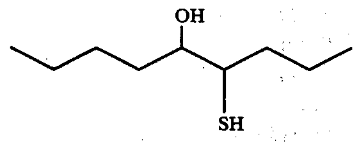 | Grapefruit aroma with green pepper nuance. |
| 5-mercapto-6-undecanone | 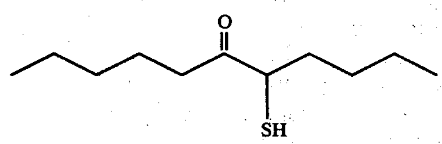 | Grapefruit aroma with vetiver nuances. |
| 5-mercapto-6-undecanol | 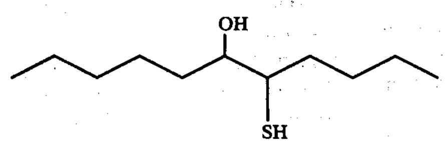 | Grapefruit, buchu oil-like aroma with minty nuances. |
| 3-mercapto-2,6-dimethyl-4-heptanone | 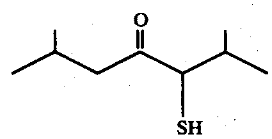 | Powerful green, tart grapefruit aroma with concord grape nuance. |
| 3-mercapto-2,6-dimethyl-4-heptanol | | Green, fruity aroma having concord grape and grapefruit oil-like nuances. |

One or more of the aforementioned α-oxy(oxo)mercaptans having the structure:

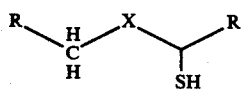

wherein X is one of:

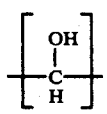

or

and R is one of ethyl, 1-propyl, 2-propyl or 1-butyl is an olfactory agent and can be incorporated into a wide variety of compositions, each of which will be enhanced or augmented by its grapefruit oil-like and/or green fruity and/or concord grape-like and/or buchu leaf oil-like and/or minty notes. The α-oxy(oxo)mercaptans or mixtures of α-oxy(oxo)mercaptans can be added to perfume compositions as pure compounds or can be added to mixtures of materials in fragrance imparting compositions to provide a desired fragrance character to a finished perfume material. The perfume and fragrance compositions obtained according to this inventin are suitable in a wide variety of perfume articles and can also be used to enhance, modify or reinforce natural fragrance materials. It will thus be appreciated that the α-oxy(oxo)mercaptans of our invention is (are) useful as olfactory agent(s) and fragrance(s).

The term "perfume composition" is used herein to mean a mixture of compounds, including, for example, natural oils, synthetic oils, alcohols, aldehydes, ketones, esters, lactones, nitriles and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh-smelling materials. Such perfume compositions of our invention can be used in conjunction with carriers, vehicles, solvents, dispersants, emulsifiers, surface-active agents, aerosol propellants and the like.

In perfume compositions the individual components contribute their particular olfactory characteristics, but the overall effect of the perfume composition will be the sum of the effect of each ingredient. Thus, one or more of the α-oxy(oxo)mercaptans of our invention can be used to alter, augment, modify or enhance the aroma characteristics of a perfume composition or a perfumed article, for example, by highlighting or moderating the olfactory reaction contributed by another ingredient of the composition.

The amount of one or more of the α-oxy(oxo)mercaptans of our invention which will be effective in perfume compositions depends upon many factors, including the other ingredients, their amounts and the effects which are desired. It has been found that perfume compositions containing as much as 2% or as little as 0.1 ppm (0.00001%) by weight of the mixtures or compounds of this invention, or even less can be used to impart a buchu leaf oil-like aroma or a grapefruit oil-like aroma to soaps, cosmetics and other products. The amount employed will depend upon considerations of cost, nature of the end product, the effect desired in the finished product, and the particular fragrance sought.

One or more of the α-oxy(oxo)mercaptans of our invention as disclosed herein can be used alone, in a fragrance modifying composition, or in a perfume composition as an olfactory component in detergents (anionic detergents, cationic detergents, and nonionic detergents) and soaps; space deodorants; perfumes; colognes, bath preparations such as bath oil, bath salts; hair preparations such as lacquers, brilliantines, pomades, and shampoos; cosmetic preparations such as creams, deodorants, hand lotions, sun screens; powders such as talcs, dusting powders, face powders and the like. When one or more of the α-oxy(oxo)mercaptans of our invention is used in perfumed articles such as the foregoing, it can be used in amounts of 0.5 ppm (0.00005%) or lower. Generally, it is preferred not to use more than about 2% in the finished perfumed article, since the use of too much will tend to unbalance the total aroma and will needlessly raise the cost of the article.

The following examples serve to illustrate embodiments of the invention as it is now preferred to practice it. It will be understood that these examples are illustrative and the invention is to be considered restricted thereto only as indicated in the appended claims.

EXAMPLE I

Part A

PREPARATION OF 3-CHLORO-4-HEPTANONE

Reaction:

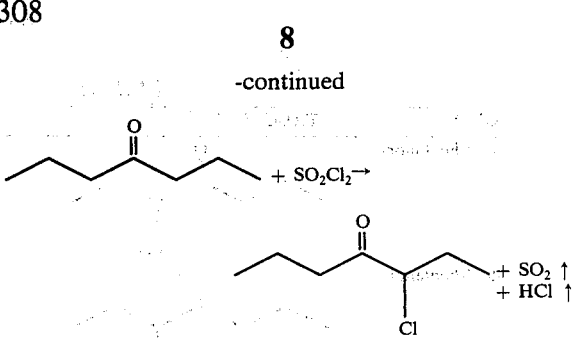

Into a 3000 ml, three-necked, round-bottom flask, equipped with mechanical stirrer, 500 ml addition funnel, "Y-tube," pot thermometer and gas outlet tube with rubber tubing leading over a stirring solution of 10% sodium hydroxide is added 1000g 4-heptanone. Addition of 434 g of $SO_2Cl_2$ drop-wise into the 4-heptanone is commenced while maintaining the pot temperature in the range of 22°–34° C and is continued over a period of two hours. A water aspirator vacuum is applied to the reaction mass in order to pull the acidic gases, sulfur dioxide and hydrogen chloride, over the NaOH solution.

The reaction mass is periodically sampled using GLC analysis until such time as about 25% mono-chlorinated ketone product is found to be present.

While maintaining the reaction mass at 15° C, 1000 ml saturated sodium chloride is added to the mixture, and the mixture is then stirred for a period of 10 minutes. The reaction mass is then transferred to a 5-liter separatory funnel and shaken well, whereupon the organic and aqueous phases separate. The lower aqueous phase (approximately 1000 ml) has a pH of about 1. The upper organic phase is washed with 700 ml saturated sodium bicarbonate solution to a pH of 6–7. The organic phase is then dried over 50 grams anhydrous sodium sulfate and filtered yielding a yellow oil weighing 1063 grams. The organic layer is determined to contain 24.94% chlorinated ketone and 68.12% original ketone starting material. This material is then vacuum distilled by first adding it to a 2000 ml, three-necked, round-bottom flask equipped with a 2.5 × 60 cm vacuum jacketed column packed with 6 mm Raschig Rings, and equipped with an automatic reflux head, a pot thermometer, a heating mantle, a vacuum pump and a dry-ice trap. Fractionation data is as follows:

| Vacuum (mmHg) | Pot Temp. | Vapor Temp. | Weight of Fraction | Cut. No. | Reflux Ratio |
|---|---|---|---|---|---|
| 62 | 80 | 71 | 51.0 g | 1 | 60:40 |
| 62 | 81.5 | 71 | 149.0 g | 2 | 40:60 |
| 58 | 82.5 | 70 | 157.5 g | 3 | 30:70 |
| 59 | 89.5 | 70 | 175.0 g | 4 | 30:70 |
| 59 | 96 | 75 | 110 g | 5 | 30:70 |
| 59 | 100 | 80 | 24.5 g | 6 | 50:50 |
| 58 | 101 | 90 | 16.0 g | 7 | 50:50 |
| 58 | 102 | 94 | 37.5 g | 8 | 30:70 |
| 55 | 103 | 94 | 144.5 g | 9 | 30:70 |
| 54 | 110 | 95 | 85.0 g | 10 | 30:70 |
| 54 | 119 | 102 | 28.0 g | 11 | 30:70 |
| 15 | 140 | 80 | 45.0 g | 12 | 30:70 |

GLC analysis on each of custs 5–12 (conditions 8 inches × ¼ inch SE-30 column) yields the following information:

| Cut No. | Percent low Boilers | Percent 4-Heptanone | Percent 3-Cl 4-Heptanone | Percent High Boiler (A) | Percent High Boiler (B) | Percent High Boiler (C) | Percent High Boiler (D) |
|---|---|---|---|---|---|---|---|
| 5 | 0.09 | 96.15 | 2.97 | — | — | — | — |
| 6 | | | | | | | |
| 7 | | 50% | 50% | | | | |
| 8 | — | 9.28 | 87.09 | 2.43 | 0.57 | — | — |
| 9 | — | trace | 95.78 | 3.22 | 1.00 | — | — |
| 10 | — | — | 91.38 | 4.89 | 3.34 | 0.21 | — |
| 11 | — | — | 69.14 | 7.27 | 19.88 | 3.71 | — |
| 12 | — | — | 8.32 | 2.07 | 49.28 | 39.69 | 0.47 |

Cuts 8, 9, and 10 are blended (weight 266.5 gms) and are analyzed by GLC as follows:

| | |
|---|---|
| 0.95% | 4-heptanone |
| 93.89% | 3-chloro-4-heptanone |
| 3.60% | high boiler A |
| 1.57% | high boiler B |

Part B

PREPARATION OF 3-MERCAPTO-4-HEPTANONE

Reaction:

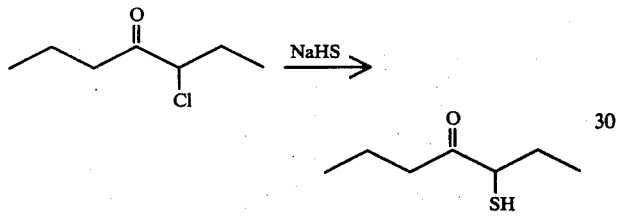

Into a 50 ml, three-necked, round-bottom flask, equipped with magnetic stirrer, pot thermometer, six inch distillation column with gas outlet at top attached to rubber tubing leading above stirring solution of 10% sodium hydroxide solution, gas inlet tube (for hydrogen sulfide bubbling), gas bubbler, empty trap between hydrogen sulfide cyclinder and bubbler, hydrogen sulfide cyclinder and isopropanol/dry-ice bath is added a solution of 1.62 g sodium methoxide dissolved in 13.5 ml anhydrous methanol. The sodium methoxide solution is cooled to −10° C and the hydrogen sulfide bubbling is commenced below the surface of the sodium methoxide solution. The reaction is maintained at a temperature of −5° to −10° C, while continuing the hydrogen sulfide bubbling and stirring the reaction mass for a period of 1½ hours. At this point, 5 ml of the cold sodium hydrosulfide solution is transferred to a 25 ml Erlenmeyer flask equipped with magnetic stirrer, dry nitrogen flow, pot thermometer, and isopropanol/dry-ice bath. At −4° to 0° C, 0.75 g (0.005 moles) of 3-chloro-4-heptanone is added dropwise over one minute using a pipette. After all of the chlorinated ketone is added, a heavy solid precipitate forms which is stirred at 0° C for 15 minutes, then allowed to warm to 23° C over an additional 50 minute time period. About 4 ml of 10% sodium hydroxide solution is then added to the reaction mass while stirring under a nitrogen blanket. Unreacted chloro ketone is extracted with 7 ml of methylene chloride and separated. The basic aqueous phase is acidified to a pH of 2 with 10% aqueous hydrochloric acid. The oil out is extracted twice with 10 ml methylene chloride. The methylene chloride extracts are combined, washed with saturated sodium chloride solution, dried and concentrated to yield 0.55 gms of product. GLC, IR and NMR analyses of trapped product yield the information that the product is 3-mercapto-4-heptanone.

The NMR spectrum is set forth in FIG. 1. The infra-red spectrum is set forth in FIG. 2.

The NMR analysis is as follows:

| | | |
|---|---|---|
| 1.04 ppm (t) | $CH_3-C-C-\overset{O}{\underset{\|}{C}}-$ | |
| 1.00 (t) | $CH_3-C-\underset{\underset{S-}{\|}}{C}-\overset{O}{\underset{\|}{C}}-$ | 6 H |
| 2.20–1.40 (m) | $-CH_2-$ $-SH$ | 5 H |
| 2.62 (m) | $-CH_2-\overset{O}{\underset{\|}{C}}-$ | 2 H |
| 3.26 (m) | $O=C-CH-S-$ | 1 H |

The infra-red analysis is as follows:
1130 cm$^{-1}$, 1360, 1370, 1400, 1450, 1705, 2540, 2870, 2930, 2960.

Part C

PREPARATION OF 3-MERCAPTO-4-HEPTANOL

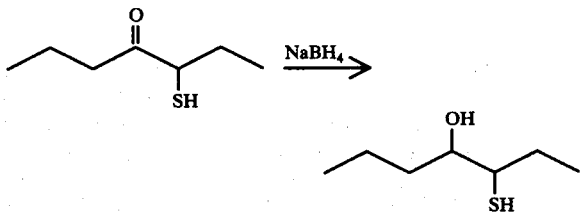

Into a 25 ml, round-bottom flask, equipped with magnetic stirrer, nitrogen inlet tube, gas outlet tube, dry-ice/acetone bath and reflux condenser is added 2.5 ml of a 95% ethanolic solution containing 0.06 gms of sodium borohydride (0.0015 moles). While maintaining the reaction mass at a temperature of between 25° and 35° C over a period of about 5 minutes, 0.44 gms (0.003 moles) of 3-mercapto-4-heptanone in 95% ethanol (2.5 ml) is added to the sodium borohydride solution. During this time, the reaction mass is stirred under a blanket of dry nitrogen.

The reaction mass is then continued to be stirred for a period of 3 hours at which time the reaction mixture is concentrated on a rotary evaporator using water aspirator vacuum to 3 ml of a thick slurry. To the slurry is added 10 ml water with stirring, and the solid then dissolves. The aqueous solution is then acidified to a pH of 6 with 4% aqueous hydrochloric acid, at which time the reaction mass exists in two phases; an aqueous phase and an organic phase. The organic phase is extracted with two 10 ml portions of methylene chloride. The extracts are combined, dried over anhydrous sodium sulfate, gravity filtered and concentrated on a rotary evaporator to yield a yellow oil weighing 0.3 gms. GLC analysis (conditions: 8 inches × ¼ inch SE-30 column) indicates 96.3% 3-mercapto-4-heptanol. NMR and IR analyses of trapped product confirm the structure of this material.

The NMR spectrum is set forth in FIG. 3. The IR spectrum is set forth in FIG. 4.

The NMR analysis is as follows:

| 1.28–0.92 | $CH_3$— + —SH | 7 H |
| 1.48 (m) | —$CH_2$— | 6 H |
| 1.96 (s) | OH | 1 H |
| 2.74 (m) | HC—S— | 1 H |
| 3.58 (m) | HC—O— | 1 H |

The infra-red analysis is as follows:
1000 cm$^{-1}$, 1050, 1070, 1110, 1130, 1280, 1370, 1450, 2540, 2860, 2920, 2950, 3400.

Material prepared similarly to above example was vacuum distilled yielding 98.5% pure product. B.P. 65°–68° C at 3 mm Hg. The thus-distilled material has the same physical properties as set forth for 3-mercapto-4-heptanol.

EXAMPLE II

Part A

PREPARATION OF 4-CHLORO-5-NONANONE

Reaction:

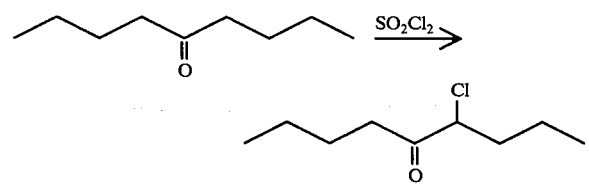

Into a 250 ml, three-necked, round-bottom flask, equipped with magnetic stirrer, six inch Vigreux column (with gas outlet to vacuum), cold water bath, pot thermometer, water aspirator vacuum and 50 ml addition funnel are placed 99 gms of 5-nonanone. 31.6 gms (18.7 ml; 0.234 moles) of $SO_2Cl_2$ are added dropwise from the addition funnel over a period of one hour while maintaining the reaction mass at a temperature of between 24° and 27° C. Water aspirator vacuum is applied to the reaction flask while stirring, in order to remove acidic gases.

The reaction mass is then warmed to 30° C and evaporated on a rotary evaporator.

The weight of crude material is 108 gms and contains 73% nonanone, and 21.4% of 4-chloro-5-nonanone.

A 250 ml, three-necked, round-bottom flask, equipped with magnetic stirrer, 1.3 × 30 cm distillation column, packed with a 6 mm Raschig Rings, reflux head, heating mantle, pot thermometer, vacuum pump, and dry-ice/isopropanol trap is used in order to distill the chlorononanone from the reaction mass. The 4-chloro-5-nonanone is then distilled at a temperature from 105°–108° C and pressure of 22.5–23 mm Hg yielding 16.7 gms of product. The material is used in Part (B), supra.

Part B

PREPARATION OF 4-MERCAPTO-5-NONANONE

Reaction:

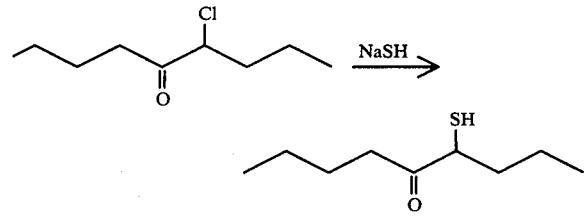

Into a 250 ml, three-necked, round-bottom flask equipped with magnetic stirrer, pot thermometer, 6 inch distillation column with gas outlet at top with rubber tubing leading above a 10% sodium hydroxide solution, a gas inlet tube (sub-surface), a gas bubbler, an empty trap between the hydrogen sulfide cylinder and bubbler, a dry-ice/isopropanol bath, and a 10 ml addition funnel, the following materials are added with stirring at 25° to 40° C:

40 ml anhydrous methanol;
4.88 gms sodium methylate (0.0903 moles).

While maintaining the temperature of the reaction mass at between −5° and −15° C addition of hydrogen sulfide is commenced, bubbling the hydrogen sulfide below the surface of the reaction mass. The hydrogen sulfide bubbling is continued for a period of two hours at whichtime it is ceased and addition of the 4-chloro-5-nonanone produced in Example I (A), supra, is commenced. The 4-chloro-5-nonanone is added over a period of 10 minutes while maintaining the reaction mass at a temperature of between −9° and −10° C.

The reaction mass is then stirred at 0° C, while hydrogen sulfide addition continues for a period of one hour.

The reaction mass is then concentrated to a yellow solution containing a white solid precipitate on a rotary evaporator to 15 ml. 35 ml water is then added with stirring followed by 35 gms of a 10% aqueous sodium hydroxide solution. Stirring is continued for a period of 10 minutes while maintaining the resulting mixture at a temperature of between 24° and 27° C. The resulting basic aqueous solution is then extracted with two portions (35 ml each) of methylene chloride and the extracts are combined, dried, and concentrated yielding an oil weighing 1.1 gms. The aqueous solution is then acidified to a pH of 1–2 using 42 ml 10% hydrochloric acid while being cooled to 25°–30° C. It is then extracted with four 25 ml portions of methylene chloride and the extracts are combined and washed with two 30 ml portions of saturated sodium chloride. The methylene chloride extracts are dried over anhydrous sodium sulfate, gravity filtered, and concentrated on a rotary evaporator to yield a light yellow oil having a weight of 6.6 gms.

GLC, IR and NMR analyses yield the information that this light yellow oil contains 94.36% 4-mercapto-5-nonanone.

The NMR spectrum is set forth in FIG. 5. The infrared spectrum is set forth in FIG. 6.

The NMR analysis is as follows:

| | | |
|---|---|---|
| 0.94 ppm (t) | $CH_3-CH_2-$ | 6 H |
| 1.72 (d) 2.04–1.18 (m) | SH $-CH_2-$ | 9 H |
| 2.60 (m) | $-CH_2-\overset{O}{\underset{\|}{C}}-$ | 2 H |
| 3.32 (m) | $-\overset{O}{\underset{\|}{C}}-HC-S-$ | 1 H |

The infra-red analysis is as follows:
1040 cm$^{-1}$, 1150, 1355, 1375, 1400, 1430, 1460, 1700, 2550, 2870, 2960.

Part C

PREPARATION OF 4-MERCAPTO-5-NONANOL

Reaction:

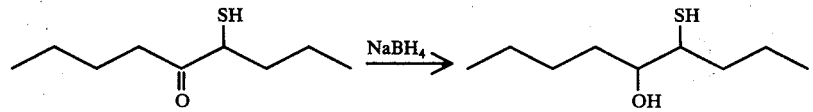

Into a 25 ml, round-bottom, three-necked flask, equipped with magnetic stirrer, pot thermometer, reflux condenser and nitrogen inlet tube is added 0.066 gms of sodium borohydride dissolved in 3 ml ethyl alcohol. Under nitrogen, 0.554 gms of 4-mercapto-5-nonanone produced according to the process of Example II (B) is dissolved in 2.5 ml of anhydrous ethanol and the resulting solution is added by pipette to the sodium borohydride solution over a period of four minutes at 23° to 34° C. The reaction mass then cools to 25° C and remains at a temperature of from 23° to 25° C for a period of one hour.

GLC analysis indicates that 74.4% of 4-mercapto-5-nonanol is formed at this point. An additional 0.033 gms of sodium borohydride in 1.5 ml ethyl alcohol is added and the reaction mass is stirred for three hours.

The reaction mass is concentrated on a rotary evaporator (using water aspirator vacuum) to a volume of about 3 ml and a thick slurry is obtained. 7 ml of water is then added and the solid dissolves yielding a turbid and oily liquid having a pH of about 10. The reaction mass is then neutralized to a pH of between four and five with 35 drops of a 10% aqueous HCl solution. The reaction mass is then extracted with two 10 ml portions of methylene chloride and the extracts are combined, washed with 3 ml water and then dried over anhydrous sodium sulfate. The methylene chloride solution is gravity filtered and evaporated on a rotary evaporator to yield 0.44 gms of a pale yellow oil. GLC analysis indicates that the resulting material is 98.2% 4-mercapto-5-nonanol.

IR and NMR analyses confirm the structure. The NMR spectrum set forth in FIG. 7. The infra-red spectrum is set forth in FIG. 8.

The NMR analysis is as follows:

| | | |
|---|---|---|
| 0.94 ppm (diffuse triplet) | $CH_3-CH_2-$ | C H |
| 1.20 (d) | SH | 1 H |
| 1.46 (broad) | $-CH_2-$ | 10 H |
| 2.06 | OH | 1 H |
| 2.80 (m) | HC—S— | 1 H |
| 3.54 (m) | HC—O— | 1 H |

The infra-red analysis is as follows:
1020 cm$^{-1}$, 1115, 1370, 1460, 2550, 2870, 2920, 2950, 3420.

EXAMPLE III

Part A

PREPARATION OF 5-CHLORO-6-UNDECANONE

Reaction:

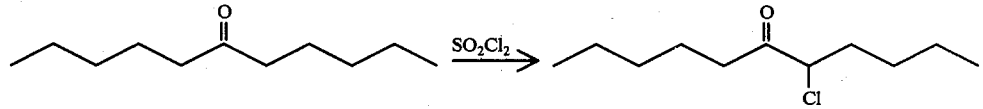

Into a 250 ml, three-necked, round bottom flask, equipped with magnetic stirrer, thermometer, 6 inch Vigreux column, with gas outlet (vacuo) at top, cold water bath, pot thermometer, water aspirator vacuum and 50 ml addition funnel is added 100 gms of 6-undecanone. 27.0 gms (16 ml; 0.200 moles) of SO$_2$Cl$_2$ is then added, dropwise, over a period of one hour while maintaining the reaction mass at a temperature of between 25° and 35° C. At the end of the one hour period, water aspirator vacuum is applied slowly to the reaction mass in order to remove acidic gases.

106 gms of the resulting reaction product (containing 22.5% of 5-chloro-6-undecanone) is then placed in a 250 ml, three-necked, round-bottom flask, equipped with a 2.0 × 30 cm distillation column, packed with ⅛ inch helices, a reflux head, a magnetic stirrer, a heating mantle, and a vacuum pump. The desired product is then distilled at a temperature of between 86° and 89° C and a pressure of 2 mm Hg. Mass spectral analysis, NMR and IR analysis confirm that the resulting product is 5-chloro-6-undecanone. This material is used in Example III (B), infra.

Part B

PREPARATION OF 5-MERCAPTO-6-UNDECANONE

Reaction:

-continued

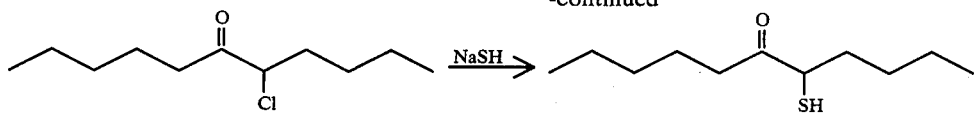

Into a 250 ml, three-necked, round bottom flask, equipped with magnetic stirrer, pot thermometer, six inch distillation column, with gas outlet at top attached to rubber tubing leading above stirring 10% sodium hydroxide solution, gas inlet tube (for hydrogen sulfide) (sub-surface), gas bubbler, empty trap between hydrogen sulfide cylinder and bubbler, hydrogen sulfide cylinder, isopropyl alcohol dry-ice bath and 10 ml addition funnel, is added 4.65 gms of sodium methoxide dissolved in 40 ml anhydrous methanol. Hydrogen sulfide is then bubbled below the surface of the sodium methoxide solution while maintaining the temperature between −3° and −15° C. While bubbling in hydrogen sulfide and maintaining the pot temperature at −3° to −8° C, 5-chloro-6-undecanone (9.05 gms) is added dropwise to the solution over a period of 15 minutes.

Hydrogen sulfide is then continued to be bubbled into the solution for a period of one hour. The reaction mass is then warmed to room temperature and concentrated on a rotary evaporator (with water aspirator vacuum applied) to a pale yellow solution containing a white solid (volume: 15 mol). 35 ml of water are added to the reaction mass, with stirring, causing the solid to dissolve. 35 gms of a 10% aqueous sodium hydroxide solution is then added to the reaction mass with stirring while maintaining the temperature at 25° C. The basic aqueous solution is then extracted with two 35 ml portions of methylene chloride, and the methylene chloride extracts are combined, dried, and concentrated yielding 1.5 gms of an oil containing about 80% 5-mercapto-6-undecanone.

The basic aqueous solution is then acidified with 50 ml 10% hydrochloric acid while maintaining the temperature at 25°–30° C. The solution is then extracted with three 35 ml portions of methylene chloride and the methylene chloride extracts are combined. The methylene chloride extracts are then washed with two 30 ml portions of saturated sodium chloride, dried over anhydrous sodium sulfate and concentrated on a rotary evaporator to a weight of 6.7 gms.

The 5-mercapto-6-undecanone is trapped out using preparative GLC (conditions: 8 inches × ¼ inch SE-30 column, programmed at 10° per minute; starting at 130° C). GLC, NMR and IR analyses confirm that the resulting product is 5-mercapto-6-undecanone.

The NMR spectrum is set forth in FIG. 9. The IR spectrum is set forth in FIG. 10.

The NMR analysis is as follows:

| 0.90 ppm (t) | CH$_3$—CH$_2$ | 6 H |
| 1.32 (broad) | —CH$_2$— | 13 H |
| 1.70 (d) | SH | |
| 2.60 (m) | —CH$_2$—C(=O)— | 2 H |
| 3.28 (m) | —C(=O)—HC—S— | 1 H |

The infra-red analysis is as follows:
1135 cm$^{-1}$, 1370, 1400, 1460, 1700, 2550, 2880, 2920.

Part C

PREPARATION OF 5-MERCAPTO-6-UNDECANOL

Reaction:

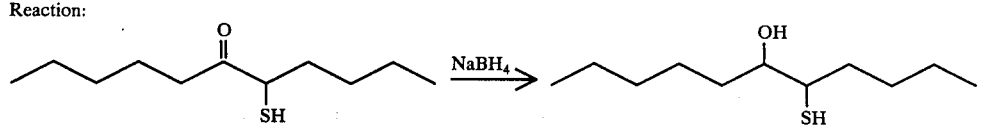

Into a 25 ml, three-necked round-bottom flask, equipped with magnetic stirrer, pot thermometer, and 6 inch Vigreux column with cotton plug, is added 0.113 gms (0.003 moles) of sodium borohydride dissolved in 5 ml ethanol. 0.61 gms of 5-mercapto-6-undecanone produced according to Example III (B), supra, dissolved in 2.5 ml anhydrous ethanol, is then added to the sodium borohydride-ethanol solution over a period of two minutes with stirring, while maintaining the reaction mass at a temperature in the range of between 23° and 38° C. The reaction mass is then stirred for a period of 2 hours while the temperature of the reaction mass remains at 24° C.

The reaction mass is then concentrated on a rotary evaporator (using a water aspirator vacuum) to a volume of about 3 ml, yielding a thick slurry. 9 ml water is then added to the resulting slurry with stirring and the solid dissolves (pH = 10). The resulting mixture is then acidified to a pH of between 2 and 3 using 10% aqueous HCl. The resulting mixture is then extracted with two 10 ml portions of methylene chloride, and the methylene chloride extracts are combined and washed with 4 ml saturated chloride solution. The washed methylene chloride extracts are then dried over anhydrous sodium sulfate, gravity filtered, and concentrated using a rotary evaporator to yield a pale yellow oil, weighing 0.38 gms and having a purity of about 99% based on GLC analysis. The resulting material is then trapped out on a GLC SE-30 column (8 inches × ¼ inch column), 130°, programmed at 10° C per minute.

The NMR spectrum is set forth in FIG. 11. The IR spectrum is set forth in FIG. 12.

The NMR analysis is as follows:

| 0.97 ppm (t) | CH$_3$—CH$_2$— | 6 H |
| 0.91 (t) | CH$_3$—CH$_2$ | |
| 1.20 (d) | —SH | 15 H |
| 1.44–1.32 (broad) | —CH$_2$— | |
| 2.04 | —OH | 1 H |
| 2.78 (m) | HC—S— | 1 H |
| 3.53 (m) | HC—O— | 1 H |

The infra-red spectrum is as follows:

1020 cm$^{-1}$, 1120, 1375, 1460, 2550, 2850, 2920, 3400.

EXAMPLE IV

Part A

PREPARATION OF 2,6-DIMETHYL-3-CHLORO-HEPTANONE-4

Reaction:

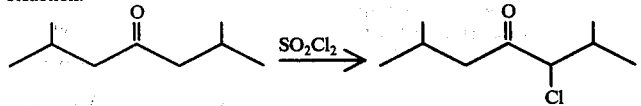

Into a one-liter, three-necked, round-bottom flask, equipped with a "Y-tube", pot thermometer, mechanical stirrer, 125 ml additional funnel, gas outlet tube, cold water bath, and water aspirator vacuum is placed 356 gms of 2,6-dimethyl-4-heptanone. 67.5 gms (0.5 moles) of $SO_2Cl_2$ is then added to the ketone, with stirring, while maintaining the reaction mass at a temperature of between 23° and 35° C, over a period of 1 hour.

At the end of the addition of the $SO_2Cl_2$, most of the acidic gases are removed using water aspirator vacuum. The reaction mass is then transferred to a one-necked, 1-liter round-bottom flask and evaporated on a rotary evaporator using water aspirator vacuum yielding a crude product weighing 371 gms. This crude material is then transferred to a 500 ml, three-necked, round-bottom flask, equipped with 2.0 × 30 cm column, packed with ⅛ inch helices, reflux head, magnetic stirrer, heating mantle, and vacuum pump. The 2,6-dimethyl-3-chloro-heptanone-4 is then distilled at a vapor temperature of 106°–107° C and a pressure of 45–46 mm Hg, yielding 37 gms of product.

Mass spectral, NMR and IR analyses confirm that the resulting material is 2,6-dimethyl-3-chloro-heptanone-4. This material is used in the process of Example IV (B), infra.

Part B

PREPARATION OF 2,6-DIMETHYL-3-MERCAPTO-HEPTANONE-4

Reaction:

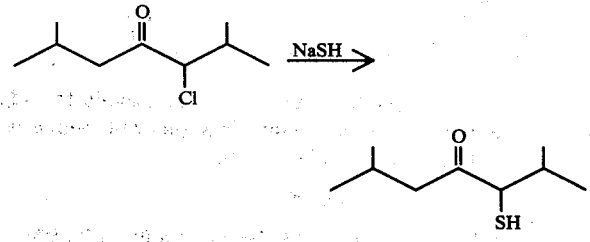

Into a 250 ml, three-necked, round-bottom flask, equipped with magnetic stirrer, pot thermometer, 6 inch Vigreux distillation column with gas outlet at top leading over 200 ml of a 10% aqueous sodium hydroxide solution, a hydrogen sulfide gas inlet tube (sub-surface), a "Y-tube", a 50 ml additional funnel, gas bubbler, a dry-ice/isopropyl alcohol bath, and a cold water bath, is added 11.6 gms of sodium methylate dissolved in 90 ml anhydrous methanol. While maintaining the temperature at between −5° and −10° C, hydrogen sulfide bubbling is commenced and continued over a period of two hours. At the end of the two hour period, while continuing hydrogen sulfide bubbling, 2,6-dimethyl-3-chloro-heptanone-4 (18.2 gms) is added to the solution while maintaining the reaction temperature at between −5° and −9° C. The addition of the chloro ketone takes place over a period of 13 minutes. Hydrogen sulfide bubbling is continued for a period of 4 hours while maintaining the reaction mass at temperatures of between 0° and 26° C (25°–26° C for the last 1.5 hours).

The resulting reaction mass is then concentrated to a yellow solution containing a white solid (25 ml volume) on a rotary evaporator to which is applied a water aspirator vacuum. 85 ml of distilled water is added to the reaction product with stirring while maintaining the reaction mass at 25° C whereupon the solid dissolves yielding a turbid yellow solution. 85 gms of a 10% aqueous sodium hydroxide solution is then added to the reaction mass while maintaining same at 25°–28° C (pH = 10–11). The reaction mass is then extracted with two 70 ml portions of methylene chloride and the methylene chloride extracts are combined, dried and concentrated yielding 1.7 gms of an oil.

The basic aqueous solution is then acidified with 115 ml aqueous 10% hydrochloric acid to a pH of between one and two. The resulting acidified solution is extracted with four 50 ml portions of methylene chloride and the methylene chloride extracts are combined and washed with two 35 ml portions of saturated sodium chloride and dried over anhydrous sodium sulfate. The resulting material is gravity filtered and concentrated on a rotary evaporator to yield 15.5 gms of a pale yellow liquid containing 96.1% 2,6-dimethyl-3-mercapto-heptanone-4 as confirmed by Mass spectral, NMR and IR analyses. The reaction product is trapped using a 8 inch × ¼ inch SE-30 GLC column, programmed at 130°, at 7.5° C/minute.

The NMR spectrum is set forth in FIG. 13. The IR spectrum is set forth in FIG. 14.

| The NMR analysis is as follows: | | |
| --- | --- | --- |
| 0.98 | methyl protons | 12 H |
| 1.62 | —SH | 1 H |
| 2.12 | methine protons | 2 H |
| 2.46 | $\underset{\underset{CH_2-C-}{\parallel}}{O}$ | 2 H |
| 3.10 | HC—S | 1 H |

The infra-red analysis is as follows:
1040 cm$^{-1}$, 1365, 1375, 1465, 1705, 2550, 2870, 2920, 2960.

13.25 gms of material produced according to this example is placed in a 25 ml, three-necked, round-bottom, equipped with a 1.6 × 15 cm Vigreux column, equipped with a magnetic stirrer, reflux head, heating mantle and vacuum pump. The material is distilled at a vapor temperature of 77.5°–78° C and a vacuum of 6 mm Hg, and the thus-distilled material has the same physical properties as set forth above, for 2,6-dimethyl-3-mercapto-heptanone-4.

Part C

PREPARATION OF 2,6-DIMETHYL-3-MERCAPTO-HEPTANOL-4

Reaction:

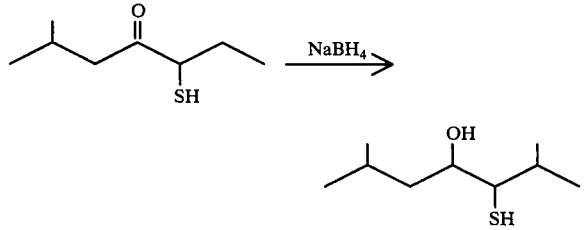

Into a 25 ml, round-bottom flask, equipped with thermometer, 15 cm Vigreux column fitted with cotton plug, and magnetic stirrer, is added 0.1 gms of sodium borohydride dissolved in 4.5 ml ethanol. While maintaining the reaction mass at a temperature of between 25° and 36° C, and over a period of six minutes, the 2,6-dimethyl-3-mercapto-haptanone-4 produced in Example IV (B), supra (0.53 gms dissolved in 2.5 ml anhydrous ethyl alcohol) is added to the reaction mass with stirring. The reaction mass is then maintained at a temperature of 25°–65° C (intermittent heating to 65° C) for a period of 11 hours, at which time it is determined by GLC analysis to contain 51.0% 2,6-dimethyl-3-mercapto-heptanol-4. (An additional 0.3 gms of sodium borohydride in 7 ml of ethanol was added during this time period).

The reaction mass is then concentrated on a rotary evaporator (to which is applied a water aspirator vacuum) to a volume of 2 ml (thick slurry). 10 ml water is added and the solid dissolves yielding a turbid aqueous solution. The resulting solution is acidified to a pH of 1–2 with approximately 2 ml, 10% hydrochloric acid. The product is then extracted with two 10 ml portions of methylene chloride and the extracts are combined and washed with 8 ml saturated sodium chloride solution, dried over anhydrous sodium sulfate, gravity filtered and concentrated on a rotary evaporator to yield 0.23 gms of an oil, containing 51% of 2,6-dimethyl-3-mercapto-heptanol-4.

The resulting product is trapped out on a GLC column (conditons: 8 inches × ¼ inch SE-30 column, programmed at 130° at 7.5° C per minute).

The NMR Spectrum is set forth in FIG. 15. The IR Spectrum is set forth in FIG. 16.

| The NMR analysis is as follows: | | |
|---|---|---|
| 1.00 ppm | Methyl protons | 12 H |
| 1.48–2.10 | $-CH_2-\ +\ H\overset{\vert}{\underset{\vert}{C}}-$ | 5 H |
| 2.20 | SH | 1 H |
| 2.62 | HC—S— | 1 H |
| 3.70 | HC—O— | 1 H |

The infra-red analysis is as follows:
1020 cm$^{-1}$, 1050, 1100, 1130, 1360, 1380, 1460, 2550, 2860, 2940, 3400.

EXAMPLE V

Both 3-mercapto-4-heptanone and 3-mercapto-4-heptanol produced according to Example I are useful in creating a synthetic grapefruit oil as follows (where 3-mercapto-4-heptanone is added at a concentration of 1 ppm and 3-mercapto-4-heptanol is added at a concentration of 20 ppm:

| INGREDIENT | I | II |
|---|---|---|
| Orange Oil Florida | 98.0 | 97.0 |
| Nootkatone (1% in Limonene) | 1.0 | 1.0 |
| 3-mercapto-4-heptanone (0.1% in Limonene) | 1.0 | — |
| 3-mercapto-4-heptanol (0.1% in Limonene) | — | 2.0 |

At the levels demonostrated, these powerful aroma chemicals twist the odor of Orange Oil to the fresh bitter grapefruit character. Even with the Nootkatone as the only additive to the Orange Oil, the grapefruit character does not come alive until the addition of either of the above compounds, the 3-mercapto-4-heptanone and the 3-mercapto-4-heptanol. The recommended preferred use level of 3-mercapto-4-heptanone and 3-mercapto-4-heptanol is in the range of from about 0.1 ppm (parts per million) up to about 50 ppm.

EXAMPLE VI

A 0.1% solution of 3-mercapto-2,6-dimethyl-4-heptanone prepared according to Example IV, Part (B) is added to Orange Oil Florida at the rate of 1%. The resulting Orange Oil aroma profile is transformed into a grapefruit-like essence.

EXAMPLE VII

The following intense, long lasting buchu-type essence having grapefruit nuances is prepared:

| INGREDIENT | PARTS BY WEIGHT |
|---|---|
| 3-mercapto-4-heptanone | 0.08 |
| α-pinene | 0.10 |
| myrcene | 0.15 |
| limonene | 1.00 |
| menthone | 1.40 |
| isomenthone | 2.60 |
| pulegone | 0.80 |
| pulegyl acetate | 0.15 |
| α-terpineol | 0.10 |
| geraniol | 0.04 |
| methyleugenol | 0.10 |
| cedryl acetate | 0.05 |
| eucalyptol | 0.30 |
| terpinen-4-ol | 0.15 |

The 3-mercapto-4-heptanone is responsible for adding the pleasant highly valuable grapefruit/buchu nuance to this otherwise bland essence.

EXAMPLE VIII

PREPARATION OF SOAP COMPOSITION

One hundred grams of soap chips are mixed with one gram of the perfume composition of Example VII until a substantially homogeneous composition is obtained. The perfumed soap composition manifests an excellent buchu leaf oil type character with warm citrusy (grapefruit-like) nuances.

EXAMPLE IX

PREPARATION OF A DETERGENT COMPOSITION

A total of 100 grams of a detergent powder (essentially water soluble non-ionic detergent and stable laundry enzyme as described in U.S. Pat. No. 3,953,353, issued on Apr. 27, 1976) is mixed with 0.15 grams of the perfume composition of Example VII until a substantially homogeneous composition is obtained. This composition has an excellent buchu leaf oil-like aroma with strong citrusy nuances.

EXAMPLE X
PREPARATION OF A COSMETIC POWDER COMPOSITION

A cosmetic powder is prepared by mixing in a ball mill 100 grams of talcum powder with 0.25 grams of the product obtained from the process of Example I (Part B). It has excellent grapefruit/buchu leaf oil-like aroma. A similar material having strong grapefruit-like aroma is prepared using the material produced according to Example IV, Part (B).

EXAMPLE XI
PERFUMED LIQUID DETERGENT

Concentrated liquid detergents with a strong buchu leaf oil-like aroma with intense grapefruit nuances are prepared containing 0.10%, 0.15% and 0.20% of 3-mercapto-4-heptanone. They are prepared by adding and homogeneously mixing the appropriate quantity of 3-mercapto-4-heptanone in the liquid detergent described according to British Pat. No. 1,092,149 containing 2% by weight ethylene/maleic anhydride copolymer (specific viscosity 0.5–1.0) and 0.42 weight percent methyl vinyl ethyl/maleic anhydride copolymer (specific viscosity 0.4) as stabilizer and 8% by weight of a sultaine detergent. The detergents all possess a strong buchu leaf oil-grapefruit fragrance, the intensity increasing with greater concentration of 3-mercapto-4-heptanone. A similar effect with additional minty nuances is obtained when using 2,6-dimethyl-3-mercapto-4-heptanone produced according to Example IV, Part (B).

EXAMPLE XII

The compound produced according to the process of Example IV, Part (B), 2,6-dimethyl-3-mercapto-4-heptanone, is incorporated into a cologne at a concentration of 2.5% in 85% aqueous ethanol; and into a handkerchief perfume at a concentration of 20% (in 95% aqueous ethanol). A distinct and definite strong buchu leaf oil-like aroma with intense grapefruit nuances is imparted to the cologne and to the handkerchief perfume. A substantially similar result is obtained when using 3-mercapto-4-heptanone and 3-mercapto-4-heptanol produced, respectively, according to Example I, Part (B) and Example I, Part (C).

EXAMPLE XIII

The composition of Example VI is incorporated into a cologne at a concentration of 2.5% in 85% aqueous ethanol; and into a handkerchief perfume at a concentration of 20% (in 95% aqueous ethanol). The use of the 3-mercapto-4-heptanone in the composition of Example VI affords a distinct and definite strong buchu leaf oil-like note with citrusy (grapefruit-like) nuances to the handkerchief perfume and to the cologne.

EXAMPLE XIV
USES OF α-OXY(OXO)MERCAPTANS IN PERFUMERY

The following examples set forth the uses and comparisons of several α-oxy(oxo)mercaptans of our invention.

4-mercapto-5-nonanone has a green, minty, grapefruit note and is approximately five times stronger than its corresponding alcohol. It is specified in the table below as "compound I".

4-mercapto-5-nonanol specified as "compound II" in the table set forth below, has a green pepper, grapefruit note.

2,6-dimethyl-3-mercapto-heptanol-4, specified as "compound III" in the table below, has a green, fruity, grape, grapefruit note.

2,6-dimethyl-3-mercapto-heptanone-4 specified as "compound IV" in the table below, has a powerful, green, tart, grapefruit note and is approximately ten times stronger than the alcohol.

5-mercapto-6-undecanol, specified as "compound V" in the table below, has a grapefruit, buchu note, with some vetiver nuances.

5-mercapto-6-undecanone, specified as "compound VI" in the table set forth below, has a green, grapefruit note, with woody, vetiver nuances and is approximately five times stronger than its corresponding alcohol.

The use of the above-mentioned mercapto compounds (α-oxy(oxo)mercaptans) may be demonostrated by blending them separately into the following synthetic perfume formulation (II) wherein they perform in such a way as to "twist" the odor of the Orange Oil into that of grapefruit. Each synthetic grapefruit oil, produced, however, is slightly different and unique in its own right due to the different character imparted by the mercapto ketone or alcohol.

Formulation A-G are first produced and these are separately added to synthetic perfume oiles II and III below:

| | FORMULATION | | | | | | |
|---|---|---|---|---|---|---|---|
| Ingredient | A | B | C | D | E | F | G |
| Orange Oil | 98.99 | 98.90 | 98.90 | 98.99 | 98.90 | 98.99 | 99.0 |
| Nootkatone | 1.0* | 1.0* | 1.00 | 1.00 | 1.00 | 1.00 | 1.00 |
| Compound I | 0.01 | — | — | — | — | — | — |
| Compound II | — | 0.10 | — | — | — | — | — |
| Compound III | — | — | 0.10 | — | — | — | — |
| Compound IV | — | — | — | 0.01 | — | — | — |
| Compound V | — | — | — | — | 0.10 | — | — |
| Compound VI | — | — | — | — | — | 0.01 | — |
| | 100.00 | 100.00 | 100.00 | 100.00 | 100.00 | 100.00 | 100.00 |

The synthetic oils (A-F) may be used to replace natural grapefruit oil in the following formulations I, II and III.

| | I | II | III |
|---|---|---|---|
| Oakmoss absolute 50% in Diethyl Phthalate | 20 | 20 | 20 |

-continued

|  | I | II | III |
|---|---|---|---|
| Helional | 10 | 10 | 10 |
| Hedione (Manufactured by Firmenich et Cie of Geneva, Switzerland) | 100 | 100 | 100 |
| Coumarin | 20 | 20 | 20 |
| Musk ketone | 80 | 80 | 80 |
| Isocyclocitral (10% in Diethyl Phthalate) | 10 | 10 | 10 |
| Galbanum Oil (10% in Diethyl Phthalate) | 6 | 6 | 6 |
| Rosemary Oil | 10 | 10 | 10 |
| Pine Needle Oil | 60 | 60 | 60 |
| Fir Balsam Absolute (10% in Diethyl Phthalate) | 10 | 10 | 10 |
| Grapefruit Oil | 60 | — | — |
| Benzyl Acetate | 470 | 470 | 470 |
| Linalool | 80 | 80 | 80 |
| Indol (10% in Diethyl Phthalate) | 6 | 6 | 6 |
| Undecalactone (10% in Diethyl Phthalate) | 12 | 12 | 12 |
| Ylang Ylang Oil | 32 | 32 | 32 |
| Lemon Oil | 14 | 14 | 14 |
| One of Formulations A-F contains an α-oxy(oxo)mercaptan of our invention | — | 60 | — |
| Formulation G (containing only Orange Oil and Nootkatone, but not containing any α-oxy(oxo)- mercaptan | — | — | 60 |

The addition of these synthetic oils produces a similar effect to that of natural grapefruit oil. Each fragrance has a novel difference in nuance due to the differences exhibited by the α-oxy(oxo)mercaptans of our invention. However, when the synthetic oils without the α-oxy(oxo)mercaptans of our invention are incorporated into the fragrance an entirely different effect away from the "grapefruit" effect is obtained.

BRIEF DESCRIPTION OF THE DRAWINGS

FIG. 11 represents the NMR spectrum for 5-mercapto-6-undecanol produced according to Example III (C).

FIG. 12 represents the infra-red spectrum for 5-mercapto-6-undecanol produced according to Example III (C).

FIG. 13 represents the NMR spectrum for 2,6-dimethyl-3-mercapto-heptanone-4 produced according to Example IV (B).

FIG. 14 represents the infra-red spectrum for 2,6-dimethyl-3-mercapto-heptanone-4 produced according to Example IV (B).

Figure 1:
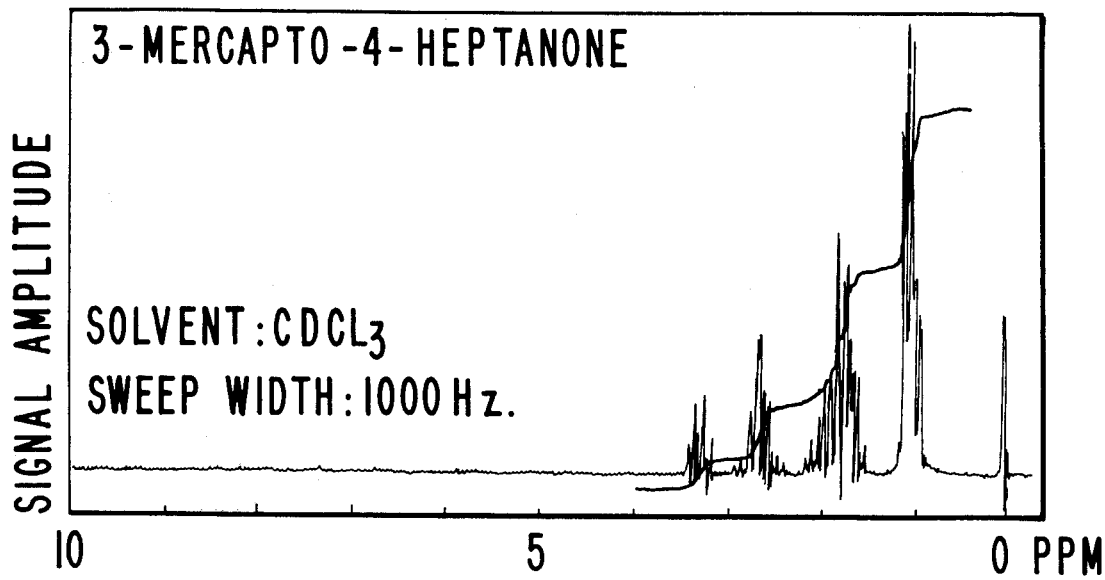
FIG. 1 represents the NMR spectrum for 3-mercapto-4-heptanone produced according to Example I (B).
Figure 2:
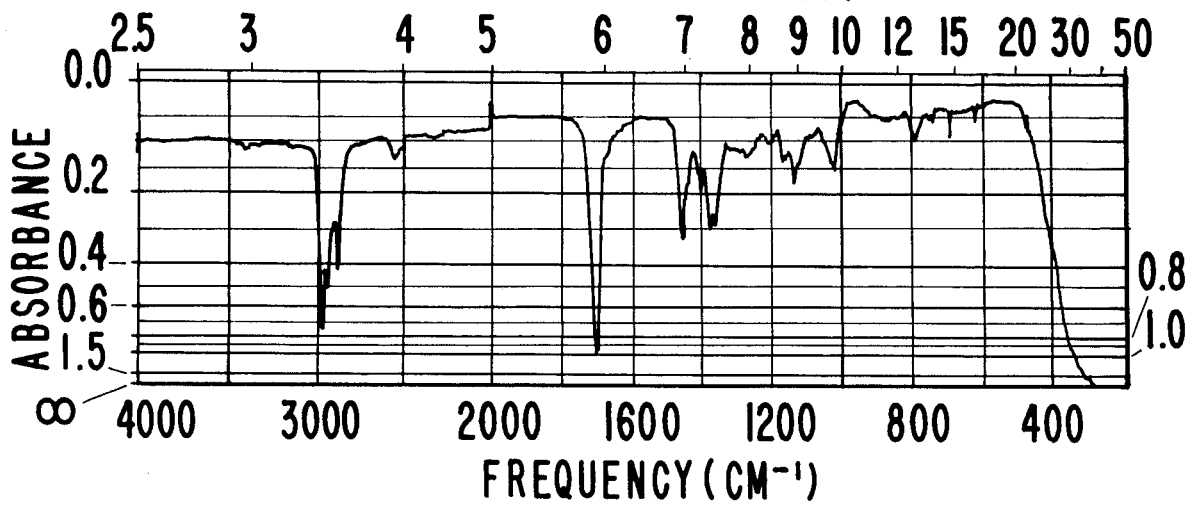
FIG. 2 represents the infra-red spectrum for 3-mercapto-4-heptanone produced according to the process of Example I (B).
Figures 3, 4:
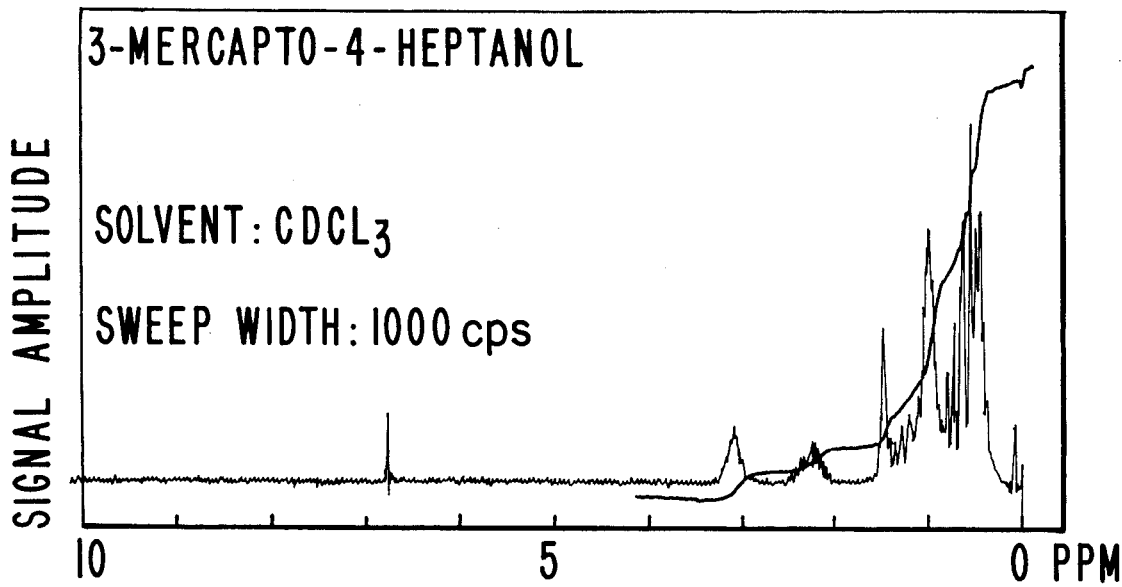
FIG. 3 represents the NMR spectrum for 3-mercapto-4-heptanol produced according to Example I (C).
FIG. 4 represents the infra-red spectrum for 3-mercapto-4-heptanol produced according to Example I (C).
Figure 5:
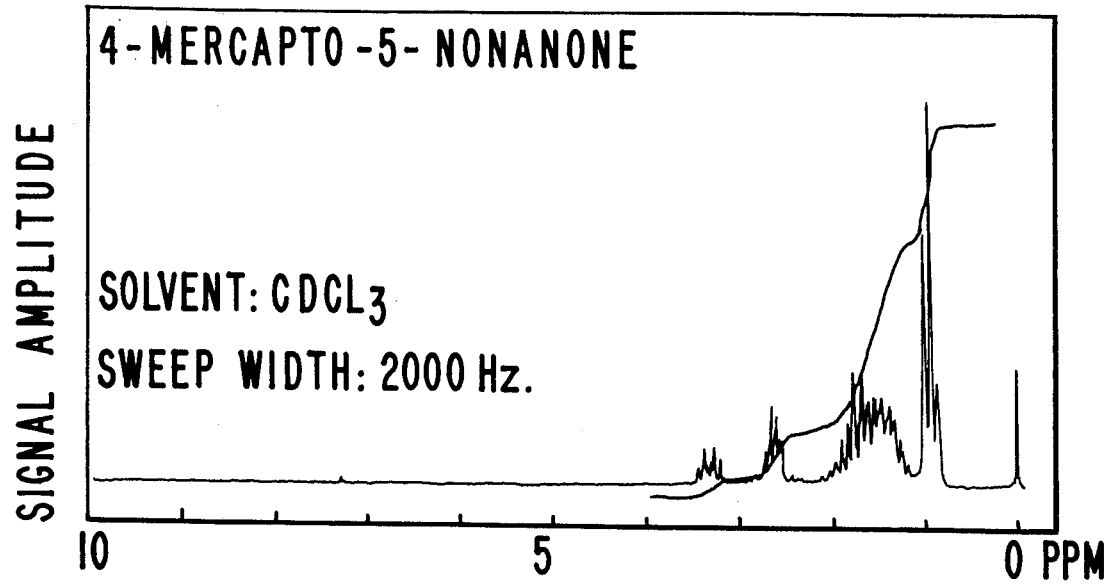
FIG. 5 represents the NMR spectrum for 4-mercapto-5-nonanone produced according to Example II (B).
Figure 6:
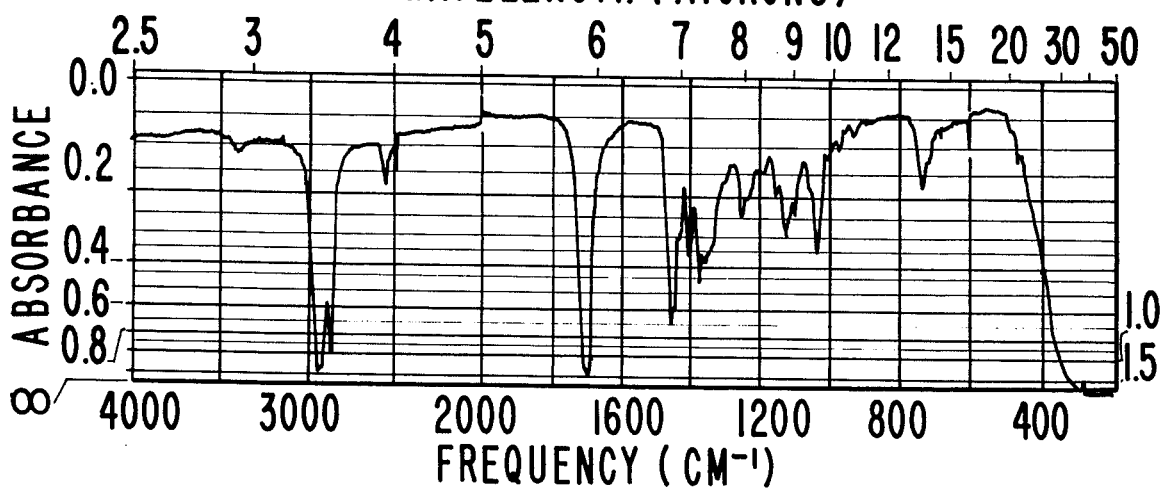
FIG. 6 represents the infra-red spectrum for 4-mercapto-5-nonanone produced according to Example II (B).
Figure 7:
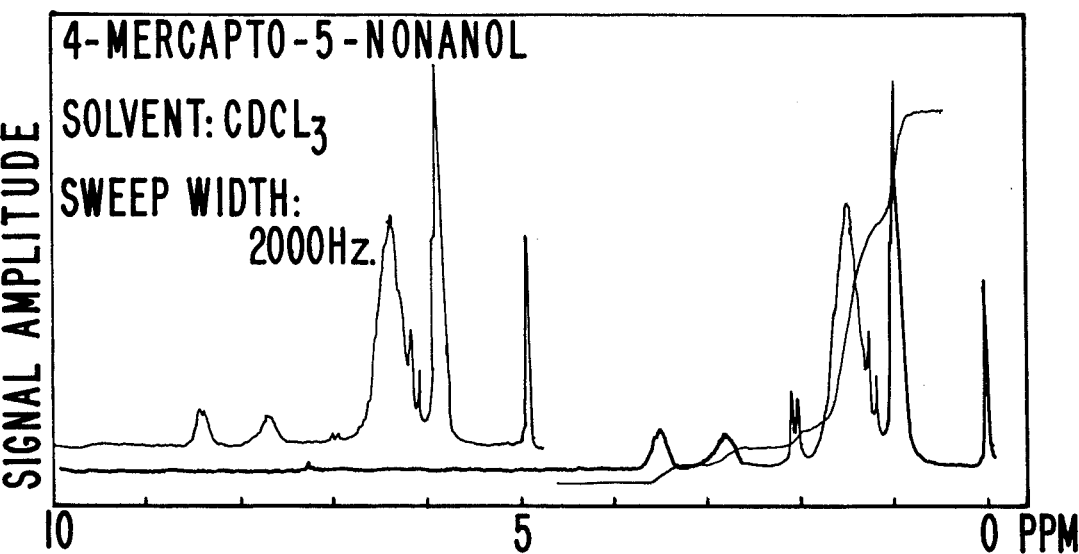
FIG. 7 represents the NMR spectrum for 4-mercapto-5-nonanol produced according to Example II (C).
Figure 8:
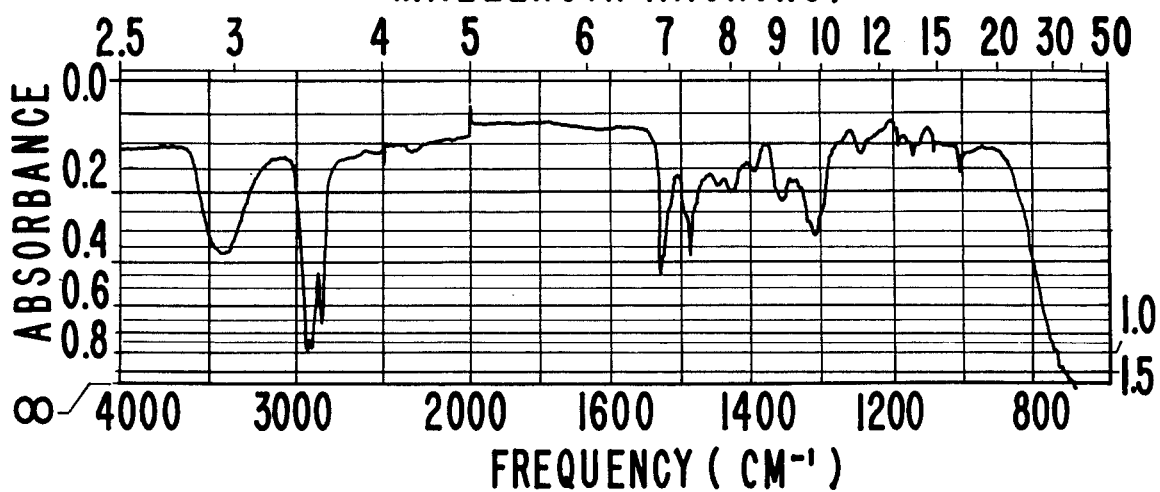
FIG. 8 represents the infra-spectrum for 4-mercapto-5-nonanol produced according to Example II (C).
Figures 9, 10:
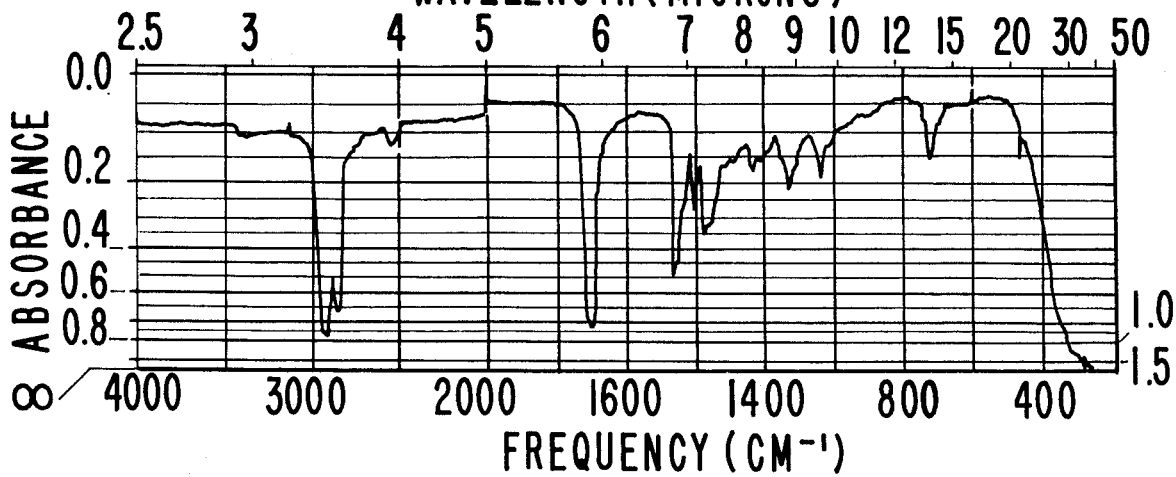
FIG. 9 represents the NMR spectrum for 5-mercapto-6-undecanone produced according to Example III (B).
FIG. 10 represents the infra-red spectrum for 5-mercapto-6-undecanone produced according to Example III (B).
Figure 15:
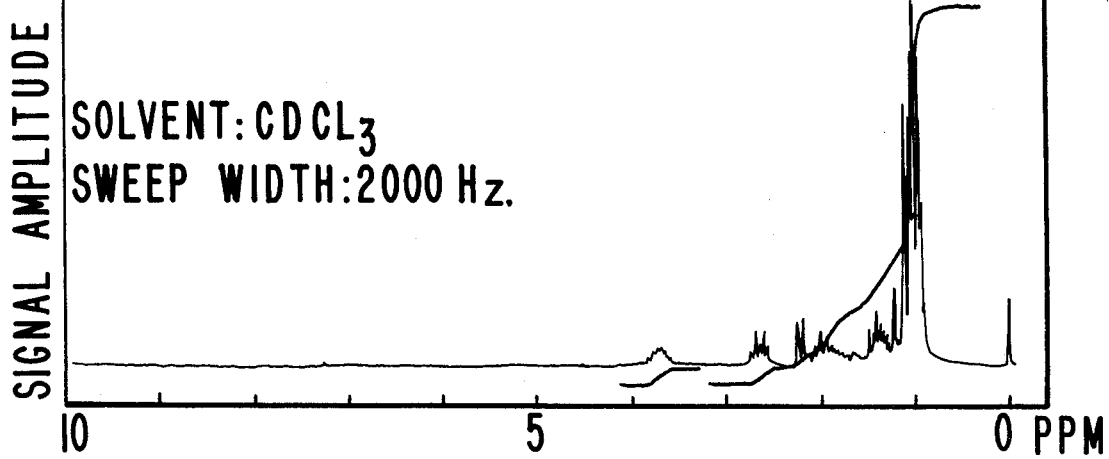
FIG. 15 represents the NMR spectrum for 2,6-dimethyl-3-mercapto-heptanol-4 produced according to Example IV (C).
Figure 16:
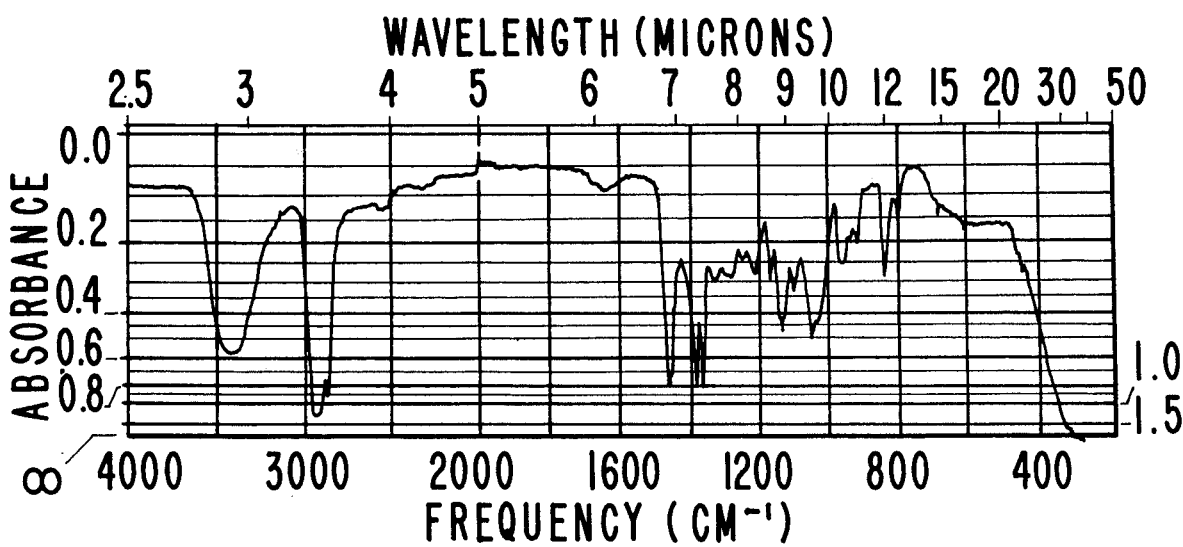
FIG. 16 represents the infra-red spectrum for 2,6-dimethyl-3-mercapto-heptanol-4 produced according to Example IV (C).

What is claimed is:

1. A perfume composition comprising at least one compound having the structure:

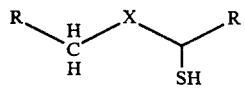

wherein R is selected from the group consisting of ethyl, 1-propyl, 2-propyl and 1-butyl; and X is the moiety:

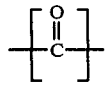

and at least one adjuvant selected from the group consisting of natural perfume oils, synthetic perfume oils, alcohols, aldehydes, ketones, esters, nitriles and lactones.

2. A process for producing a perfume composition comprising the step of admixing a composition of matter with a fragrance imparting quantity of an alpha-oxy(oxo)mercaptan having the structure:

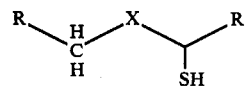

wherein R is selected from the group consisting of ethyl, 1-propyl, 2-propyl and 1-butyl; X is the moiety:

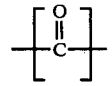

3. A cologne composition comprising an alpha-oxy(oxo)mercaptan having the structure:

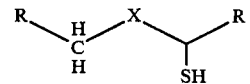

wherein R is selected from the group consisting of ethyl, 1-propyl, 2-propyl and 1-butyl; and X is the moiety

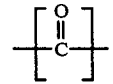

and ethanol and water.

4. The composition of claim 1 wherein R is ethyl.
5. The composition of claim 1 wherein R is 1-propyl.
6. The composition of claim 1 wherein R is 2-propyl.

7. The composition of claim 1 wherein R is 1-butyl.

8. The composition of claim 1 wherein R is ethyl.

9. The process of claim 2 wherein, in the alpha-oxy(oxo)mercaptan, R is ethyl.

10. The process of claim 2 wherein, in the alpha-oxy(oxo)mercaptan, R is ethyl.

11. The cologne of claim 3 wherein, in the alpha-oxy(oxo)mercaptan, R is ethyl.

12. The cologne of claim 3 wherein, in the alpha-oxy(oxo)mercaptan, R is 2-propyl.

* * * * *